United States Patent [19]

Potter et al.

[11] Patent Number: 5,506,097

[45] Date of Patent: Apr. 9, 1996

[54] METHOD FOR INHIBITING β-PROTEIN ENZYMATIC ACTIVITY

[75] Inventors: Huntington Potter, Boston; Usamah Kayyali, Watertown, both of Mass.

[73] Assignee: President and Fellows of Harvard College, Cambridge, Mass.

[21] Appl. No.: 179,574

[22] Filed: Jan. 10, 1994

Related U.S. Application Data

[63] Continuation-in-part of Ser. No. 819,361, Jan. 13, 1992, Pat. No. 5,338,663, which is a continuation-in-part of Ser. No. 572,671, Aug. 24, 1990, abandoned which is PCT/US93/00325, Jan. 13, 1993.

[51] Int. Cl.$^6$ .............................. C12Q 1/00; C12Q 1/46
[52] U.S. Cl. ................... 435/4; 435/19; 435/20; 435/184
[58] Field of Search ................... 435/4, 7.4, 19, 435/23, 183, 184, 210, 20

[56] References Cited

U.S. PATENT DOCUMENTS

| | | | |
|---|---|---|---|
| 4,303,592 | 12/1981 | Laura et al. | 260/543 |
| 4,358,602 | 11/1982 | Umezawa | 549/328 |
| 5,187,153 | 2/1993 | Cordell | 514/12 |
| 5,234,814 | 10/1993 | Card | 435/7.21 |
| 5,252,463 | 10/1993 | Nelson | 435/23 |
| 5,338,663 | 8/1994 | Potter | 435/4 |

FOREIGN PATENT DOCUMENTS

| | | |
|---|---|---|
| 2071661 | 9/1981 | United Kingdom . |
| 91/13904 | 9/1991 | WIPO . |
| WO92/03542 | 3/1992 | WIPO . |
| WO92/03474 | 3/1992 | WIPO . |

OTHER PUBLICATIONS

Iversen, L., The Toxicity in vitro of Beta–Amyloid Protein, Biochem J vol. 311, (1995) pp. 1–16.

Fraser, P. E., et al., "$\alpha_1$–Antichymotrypsin Binding to Alzheimer Aβ Peptides Is Sequence Specific and Induces Fibril Disaggregation In Vitro," *J. of Nurochem.*, 61(1):298–305 (1993).

Nelson, R. B. and Siman, R., "Clipsin, a Chymotrypsin–Like Protease in Rat Brain Which is Irreversibly Inhibited by α–1–Antichymotrypsin," *J of Biol. Chem.*, 265(7):3836–3842 (1990).

Nelson, R. B. and Siman, R., "Clipsin, a Chymotrypsin–Like Protease in Rat Brain Which is Irreversibly Inhibited by α–1–Antichymotrypsin," *J. Biol. Chem.*, 266(19):12796 (1991).

Abraham, C. R., et al., "A Calcium–Activated Protease From Alzheimer's Disease Brain Cleaves at the N–Terminus of the Amyloid β–Protein," *Biochem. and Biophys. Research Comm.*, 174(2):790–796 (1991).

Neve, R. L. and Potter, H., "Molecular Biology of Alzheimer Amyloid Plaque Proteins," In Brosus, Jugel and Freman, Robert T. (ed.), *Molecular Genetic Approaches to Neuropsychiatric Disease*, (Academic Press Inc., San Diego) pp. 281–305 (1991).

Potter, H., et al., "The Two Alzheimer Amyloid Components $\alpha_1$–Antichymotrypsin and β–Protein Form a Stable Complex In Vitro," *Neurobiol. of Aging*, 11(3):245 (1990).

Potter, H., et al., "The Alzheimer Amyloid Components $\alpha_1$–Antichymotrypsin and β–Protein Form a Stable Complex In Vitro," In K. Iqbal, et al. (Ed.), *Alzheimer's Disease: Basic Mechanisms, Diagnosis and Therapeutic Strategies* (NY: John Wiley & Sons Ltd.), pp. 275–280 (1991).

Yankner, B. A., et al., "Neurotrophic and Neurotoxic Effects of Amyloid β Protein: Reversal by Tachykinin Neuropeptides," *Science*, 250:279–282 (1990).

Whitson, J. S., et al., "Amyloid β Protein Enhances the Survival of Hippocampal Neurons In Vitro," *Science*, 243:1488–1490 (1989).

Potter, H., et al., "The Involvement of Proteases, Protease Inhibitors, and an Acute Phase Response in Alzheimer's Disease," *Annals NY Acad. Sci.* pp. 161–173 (1992).

Kayyali, U. S., et al., "Characterization of Amyloid Precursor Protein–Associated Serine Esterase Activity in Different Cell Lines," [From *Society for Neuroscience Abstracts*, 19 (2)], 23rd Annual Meeting, Washington, D.C., Nov. 7–12 (1993), Abstract No. 669.7.

Kayyali, U. S., et al., "Identification of adrelase–A serine hydrolase intrinsic to the Alzheimer amyloid precursor protein", *Advances in the Biosciences* 87:221–222 (1993).

*Primary Examiner*—Ralph J. Gitomer
*Attorney, Agent, or Firm*—Hamilton, Brook, Smith & Reynolds

[57] ABSTRACT

A method of inhibiting the function of β-protein, particularly enzymatic activity, such as esterase (cholinesterase) or proteinase activity, is to contact β-protein with a compound which inhibits such enzymatic activity. Examples of such inhibitors are para-amidinophenylmethanesulfonyl fluoride and Ebelactone A, which inhibit the esterase activity of amyloid precursor protein to a greater extent than the esterase activity of acetylcholinesterase.

4 Claims, 6 Drawing Sheets

| | |
|---|---|
| ALZHEIMER AMYLOID β-PROTEIN | D A E F R H D S G Y E V H H Q K L V F F A E D V G S N K • <br> G A I I G L M V G G V V I A |
| CYTOTOXIC T CELL PROTEASE | — — — A A F R G D S G G |
| CATHEPSIN G | A S F K G D S G G |
| MAST CELL PROTEASE | A A F M G D S G G |
| TRYPSIN | D S C Q G D S G G |
| CHYMOTRYPSIN | S S C M G D S G G <br> ↑ <br> ACTIVE SITE SERINE 195 |

FIG. 1

Autoradiogram

Immunoblot 1  2  3  4  5  6  7  8  9  10  11  12  13  14  15  16  17  18

1.        ACT + $^{125}$I β 1-28 + DSS
2. 65°C   ACT + $^{125}$I β 1-28 + DSS
3.        BSA + $^{125}$I β 1-28 + DSS
4.        CPK + $^{125}$I β 1-28 + DSS
5.        CA  + $^{125}$I β 1-28 + DSS
6.            + $^{125}$I β 1-28 + DSS
7.        $\overline{\text{ACT}}$ + $^{125}$I β 1-28 + DSS
8. CT +   ACT + $^{125}$I β 1-28 + DSS
9.        ACT + $^{125}$I β 1-28 + DSS
10.       ACT + $^{125}$I β 1-28
11.       ACT + $^{125}$I β 1-12 + DSS
12. CT +  ACT + $^{125}$I β 1-12 + DSS
13.       ACT + $^{125}$I β 1-12
14. CT +  ACT + $^{125}$I β 1-12
15.       ACT + $^{125}$I β 1-28
16.       ACT + $^{125}$I β 1-12
17.       ACT + $^{125}$I βPP 258-277
18.       ACT + $^{125}$I βPP Ser→Ala 3,11-Dihydroxy-4,6,8,10,12-pentamethyl-9-oxo-tetradecenoic 1,3-lactone (p-Amidinophenyl) ethanesulfonyl fluoride (p-Amidinoethyl benzyl) methanesulfonyl fluoride

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 42 amino acids
        ( B ) TYPE: amino acid
        ( D ) TOPOLOGY: linear ( x i ) SEQUENCE DESCRIPTION: SEQ ID NO:1:

```
Asp Ala Glu Phe Arg His Asp Ser Gly Tyr Glu Val His His Gln Lys
1               5                   10                  15
Leu Val Phe Phe Ala Glu Asp Val Gly Ser Asn Lys Gly Ala Ile Ile
            20                  25                  30
Gly Leu Met Val Gly Gly Val Val Ile Ala
            35                  40
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:2:

```
Ala Ala Phe Arg Gly Asp Ser Gly Gly
1               5
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:3:

```
Ala Ser Phe Lys Gly Asp Ser Gly Gly
1               5
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:4:

```
Ala Ala Phe Met Gly Asp Ser Gly Gly
1               5
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:5:

```
Asp Ser Cys Gln Gly Asp Ser Gly Gly
1               5
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:6:

-continued

```
Ser  Ser  Cys  Met  Gly  Asp  Ser  Gly  Gly
 1              5
```

METHOD FOR INHIBITING β-PROTEIN ENZYMATIC ACTIVITY

This application is a continuation-in-part of U.S. Ser. No. 07/819,361, filed Jan. 13, 1992, now U.S. Pat. No. 5,338,663, entitled "Method of Interfering With Formation of α-Antichymotrypsin-β-Protein Complex, Method of Inhibiting β-Protein Function and Compounds For Use Therein" by Huntington Potter and Usamah Kayyali which is a continuation-in-part of U.S. Ser. No. 07/572,671, filed Aug. 24, 1990, now abandoned, entitled "Method of Interfering With Formation of α-Antichymotrypsin-β-Protein Complex and Synthetic Peptides For Use Therein" by Huntington Potter (Abandoned). Priority is also claimed to PCT/US93/00325 filed Jan. 13, 1993. The teachings of these applications are incorporated by reference. Work described herein was supported by NIH Grants AG08084 and GM35967. The United States Government has certain rights in the invention.

BACKGROUND

Alzheimer's disease is a degenerative disorder of the central nervous system that results in a progressive loss of memory and other intellectual functions, such as reasoning, orientation, and judgement (R. Katzman, Banbury Report 15: Biological Aspects of Alzheimer's Disease, Cold Spring Harbor Laboratory, Cold Spring Harbor, N.Y., (1983)). Alzheimer's disease occurs in sporadic and familial forms, and in the United States, affects about 600 people for every 100,000. A characteristic aspect of the neuropathology of the disease is the occurrence of proteinaceous deposits referred to as "amyloid" in the cores of brain lesions called neuritic or senile plaques, as well as in cerebral blood vessels. The "amyloid" deposits are generally defined as 6–10 nm protein filaments with certain staining properties (Abraham, C. R. et al., Cell 52:487–501 (1988)).

Amyloid deposits are also found in the brains of aged humans, although not as extensively as in Alzheimer's disease. Further, Down's syndrome patients more than 30 or 40 years old invariably develop the symptoms and neuropathology characteristic of Alzheimer's disease.

One component of the amyloid deposits was identified as A4 amyloid or β-protein (β-protein) and is 42 amino acids long (Glenner, G. G and C. G. Wong, Biochem. Biophys. Res. Commun. 120:885–890 (1984)). This protein is apparently derived from a larger membrane-spanning precursor protein whose RNA is alternately spliced to yield several protein products (Seikoe, D. J., Science 248:1058–1060). These observations suggested that the amyloid deposits in Alzheimer's disease could result from abnormal expression or posttranslational modification or processing of a normal molecule. Also intriguing was the finding that the gene encoding the amyloid protein precursor is located on chromosome 21, suggesting a common cause for the deposits observed in Down's syndrome, caused by trisomy of chromosome 21, and Alzheimer's disease.

As mentioned above, some cases of Alzheimer's disease appear to be familial, and are inherited in an autosomal dominant fashion. Linkage analysis in four families pointed to a lesion on the long arm of chromosome 21 (St. George-Hyslop, P. H. et al., Science 238:664–660 (1987)), which correlated well with the mapping data and similarities between Down syndrome and Alzheimer disease. Recently, hereditary cerebral hemorrhage with amyloidosis of Dutch origin was reported to be linked to the APP gene, and a point mutation in the coding region of the gene was identified (Van Broeckhoven, C. et al., Science 248:1120–1122 (1990); Levy, E. et al., Science 248:1124–1126 (1990)). Patients with this disease have a form of the β-protein in amyloid deposits in meningeal and cerebral blood vessels.

However, other studies reported linkage of familial Alzheimer's disease to a locus on chromosome 21 distinct from the amyloid precursor protein (APP) gene (Tanzi, R. E. et al., Nature 329:156–157 (1987); Van Broeckhoven, C. et al., Nature 329:153–155 (1987)). Furthermore, there was no evidence of duplication of the APP gene in cases of familial or sporadic disease. In fact, studies of some families reportedly indicate no linkage to chromosome 21 (Schellenberg, G. D., Science 241:1507–1510 (1988)). These data suggest that there may be genetic heterogeneity in the cause of inherited forms of Alzheimer's disease, and other locations for the disease gene have been proposed, such as chromosome 14 (Weitkamp, L. R., Amer. J. Hum. Genet. 35:443–453 (1983)).

Thus, other components of the proteinaceous deposits in Alzheimer's disease may also be of interest and may provide clues to the cause or progress of the disease. In fact, a second component of the amyloid deposits has been characterized as $\alpha_1$-antichymotrypsin (ACT), which, interestingly, is located on chromosome 14. Abraham et al. reported the identification of the serine protease inhibitor ACT in amyloid deposits in Alzheimer's disease brain. (Abraham, C. R. et al., Cell 52:487–501 (1988).

SUMMARY OF THE INVENTION

This invention relates to a method of interfering with the interaction and/or function of $\alpha_1$-antichymotrypsin (ACT) and β-protein and, as a result, reducing the adverse effects associated with formation of a complex comprising the two or with activity of the complex components. In one embodiment, the subject invention relates to methods of interfering with the formation of a specific complex between ACT and β-protein and, thus, of reducing adverse effects resulting from complex formation, such as occurs in Alzheimer's disease. In another embodiment, the present invention relates to methods of inhibiting the function of the components of the ACT-β-protein complex. In particular, it relates to methods of inhibiting the function of β-protein, which, as shown herein, has enzymatic activity which might be of physiological relevance.

This invention relates to a novel class of synthetic peptides or peptide-like compounds which mimic a component of the specific complex which forms between the Alzheimer's β-protein and ACT, and which are useful to interfere with formation of the complex. The invention also relates to a method of treating an individual in whom such complexes form, resulting directly or indirectly in an abnormal condition or disease state, and particularly to a method of treating an individual with Alzheimer's disease. The synthetic peptides of the present invention, which inhibit complex formation between the Alzheimer's β-protein and ACT by binding to the β-protein or to ACT, can be administered to an individual in such a manner as to interfere with the ACT-β-protein interaction, and in sufficient quantity so as to have the desired effect (i.e., reduction of complex formation and the abnormal disease state).

This invention also relates to inhibitors of the enzymatic or other activity of components of the ACT-β-protein complex. In one embodiment, it relates to compositions or compounds which inhibit the activity of β-protein, β-protein precursors or β-protein fragments. As described herein, β-protein precursor proteins and β-protein fragments have been shown to have esterase activity, including cholinesterase activity (see Examples 3 and 4), and are being assessed for additional esterase or protease activities. As a result, the activity of β-protein can be inhibited by administering compositions or compounds which interfere with its cholinesterase activity or other esterase (e.g., lipase) or protease activity. Such compositions or compounds, which can be known materials or materials designed or developed specifically for inhibiting β-protein, can be administered to an individual in need of β-protein inhibition by the present method in sufficient quantities to be effective in inhibiting the β-protein activity.

A further subject of the present invention is a method of identifying β-protein inhibitors and inhibitors identified thereby. In the method, β-protein, a substrate upon which it acts (e.g., acetylthiocholine) and a potential β-protein inhibitor are combined under conditions suitable for β-protein activity; in the presence of a β-protein inhibitor, hydrolysis of the substrate does not occur or occurs to a lesser extent than would be the case in the absence of the inhibitor.

BRIEF DESCRIPTION OF THE DRAWINGS

FIG. 1 is the amino acid sequence of Alzheimer amyloid β-protein (SEQ ID NO. 1) (top row) and the active sites of the following five serine proteases: cytotoxic T cell protease (SEQ ID NO. 2); cathepsin G (SEQ ID NO. 3); mast cell protease (SEQ ID NO. 4); trypsin (SEQ ID NO. 5); and chymotrypsin (SEQ ID NO. 6).

| Delta A Rat | $y = 1.9838e-2 + 1.4096e-3x$ $R^{\wedge}2 = 0.964$ |
| Delta A Hum | $y = 2.5353e-2 + 6.5074e-4x$ $R^{\wedge}2 = 0.959$ |
| Delta A AChE | $y = 2.94853-3 + 2.8559e-3x$ $R^{\wedge}2 = 0.988$ |

Figure 5:
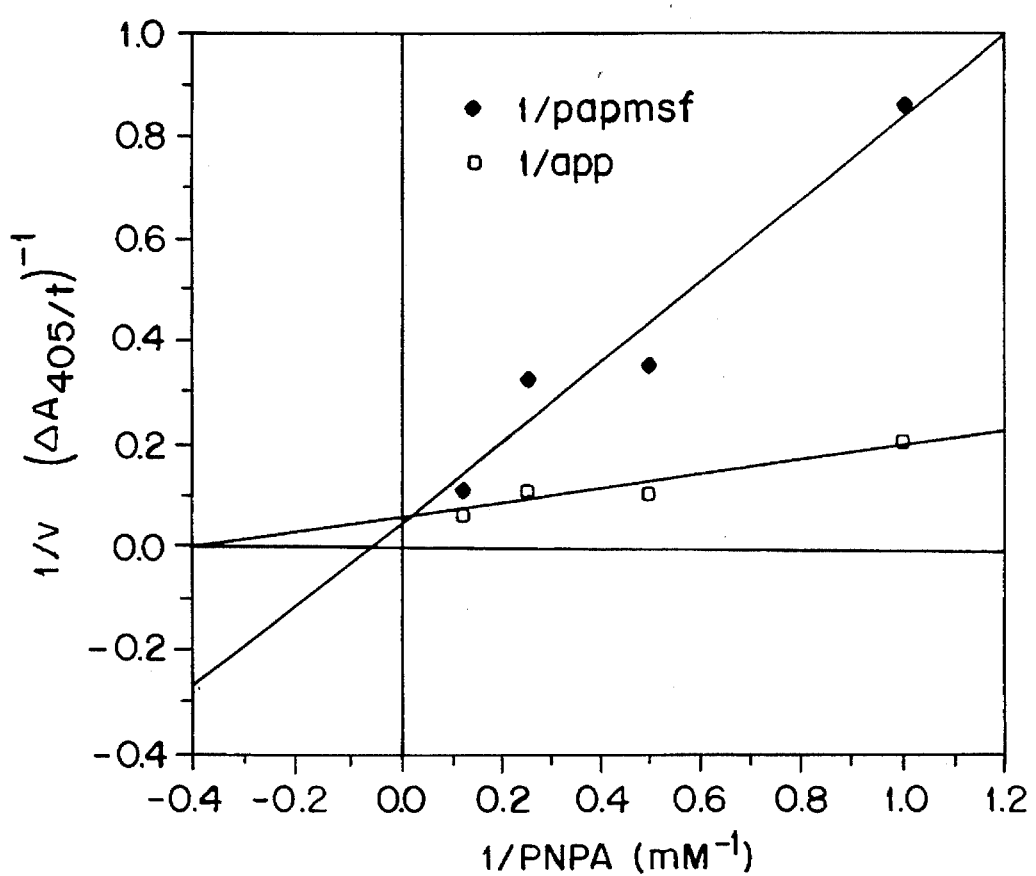
Figure 6:
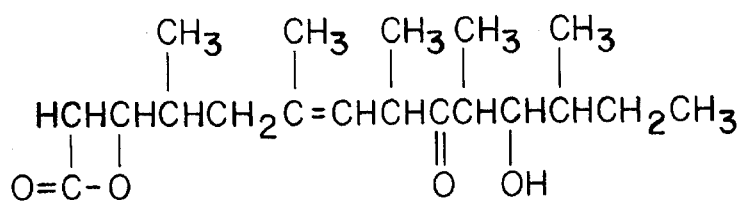
Figure 6:
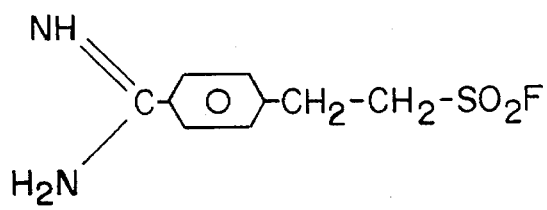
Figure 6:
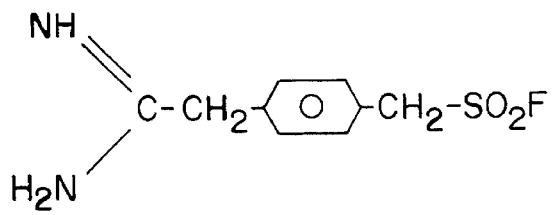

FIG. 5 is a graphic representation of the inhibition by para-amidinophenylmethanesulfonyl fluoride (pAPMSF) of the hydrolysis of various concentrations of para-nitrophenyl acetate (PNPA) by APP695-associated esterase isolated from CHO cells. The data for the reaction in the presence of pAPMSF (squares) and in the absence of pAPMSF (filled diamonds) is presented in the form of a double-reciprocal (Lineweaver-Burk) plot of i/PNPA] (ram$^{-1}$) versus i/v (where v=$\Delta A_{405}$/time). The equations for the upper (filled diamonds) and lower lines (squares), respectively, are:

$y=5.4198e-2+0.14479x$; $R^{\wedge}2=0.894$;

$y=4.5422e-2+0.79028x$; $R^{\wedge}2=0.947$;

FIG. 6 is an illustration of the structure of 3,11-dihydroxy-4,6,8,10,12-pentamethyl-9-oxotetradecenoic 1,3-lactone, a compound related to Ebelactone A, and of (p-amidinophenyl) ethanesulfonyl fluoride and (p-amidinoethyl benzyl) methane sulfonyl fluoride, two compounds which are related to pAPMSF.

DETAILED DESCRIPTION OF THE INVENTION

The protease inhibitor $\alpha_1$-antichymotrypsin (ACT) and the 42-amino acid β-protein are integral components of the brain amyloid deposits of Alzheimer's disease, Down's syndrome, and normal aging. This indicates that there is a special affinity between ACT and the β-protein, perhaps essential to amyloid formation. A basis for this association is suggested by the similarity of the N-terminus of β-protein to the active site of serine proteases.

As described herein, in vitro experiments demonstrate that ACT and β-protein form a complex that reflects the specificity and stability of a protease-inhibitor interaction. These results suggest a model for the amyloid filament and a physiological function for the β-protein. As also described herein, β-protein peptides and a β-protein precursor protein have been shown to exhibit esterase activity which might have physiological relevance. It is reasonable to expect that the activity of β-protein has a role in the toxic action of the amyloid deposits of which β-protein is a component. It is also reasonable to predict that the β-protein has other esterase or protease activity, which can be assessed using known methods, and that that enzymatic activity also has physiological relevance.

It has been demonstrated that the β-protein precursor protein termed APP695 hydrolyzes acetylthiocholine and para-nitrophenyl acetate, indicating that it has esterase activity. In addition, it has been shown that synthetic Alzheimer β-peptides 1–40 corresponding to rat and human sequences hydrolyze acetylthiocholine in a time-dependent manner and that the esterase activity is due to an intrinsic property of the β-peptide, rather than to a non-specific peptide action. As is also described, both the activity data and radiolabeling data indicate that the esterase activity observed is not due to acetylcholinesterase.

Results presented herein make it possible to design or select synthetic peptides which can be administered to an individual (introduced into cells) in order to interfere with (reduce or prevent) binding of the two components to form the complex. Such synthetic peptides include peptides and peptide-like compounds (e.g., modified or derivatized peptides) which interfere with interaction of ACT with β-protein, particularly peptides which "mimic" the active (or binding) site of serine proteases. Such peptides can be short peptides in which the amino acid sequence is sufficiently homologous with the sequence of the binding site of a serine protease or with the N-terminus of β-protein as shown in FIG. 1, that they bind with ACT. Alternatively, such peptides can include, in addition to the sequence sufficiently homologous with the serine protease binding site or β-protein region, other amino acids (e.g., one or more amino acids at either or both ends of the binding site sequence). According to the method of the present invention, a compound of the present invention is introduced into an individual in such a manner that it interferes with formation of the ACT-β-protein complex. In the present method of interfering with complex formation, a compound is administered in sufficient quantity and by an appropriate route to have a therapeutic effect (to result in decreased complex formation).

Results described herein also make it possible to design or select compositions or compounds useful for inhibiting the activity of the ACT-β-protein complex or its components. Such compositions can be, for example, agents which inhibit the enzymatic activity of β-protein, β-protein precursor protein or β-protein fragments (referred to collectively herein as β-protein), either directly or indirectly. They can be, for example, esterase inhibitors, particularly cholinesterase inhibitors, or protease inhibitors which are known agents or are designed for the purpose of inhibiting β-protein. Such inhibitors can act directly (e.g., by destroying, binding or otherwise tieing up the β-protein) or indirectly (e.g., by acting like a "decoy" substrate for the β-protein activity and, thus, protecting the physiological substrate upon which the β-protein acts). According to the method of the present invention, an inhibitor of the activity of a complex component (e.g., an inhibitor of β-protein enzymatic activity) is introduced into an individual in such a manner and in sufficient quantity to inhibit the activity and reduce (totally or partially) the adverse effects which would otherwise occur.

The following is a description of the demonstration that ACT and β-protein interact with specificity to form a stable complex in vitro and of the assessment of esterase activity of β-protein peptides and β-protein precursor proteins, of compounds which can be used to interfere with the interaction and of inhibitors of the activity of ACT-β-protein complex components, such as β-protein esterase activity. As used herein, the term β-protein includes β-protein (as described on p. 2 above), β-protein precursor proteins and β-protein fragments, present in a complex with $\alpha_1$-antichymotrypsin or in an unbound form (not in a complex with $\alpha_1$-antichymotrypsin). Identification of such compounds and the method by which they are administered are also described.

The present invention can be used in the treatment of individuals, such as those with Alzheimer's disease, in whom complex formation would otherwise occur or in whom β-protein activity would otherwise have a deleterious effect, such as excessive inactivation or destruction of acetylcholine or destruction of key proteins in surrounding tissues.

Demonstration of Formation of ACT-β-Protein complex

The extracellular amyloid filaments found in the plaques and blood vessels of Alzheimer's disease, Down's syndrome, and normal aging, contain two proteins, both intimately associated with the filaments—the 42 amino acid β-protein and the serine protease inhibitor, $\alpha_1$-antichymotrypsin (Glenner, G. G. and C. W. Wong, *Biochem. Biophys. Res. Comm.* 122:885 (1984); C. L. Masters, et al., *EMBO J.* 4:2757 (1985); D. J. Seikoe, et al., *J. Neurochem.* 46:1820 (1986); D. J. Selkoe, et al., *Science* 235:873 (1987); Abraham, C. R. and H. Potter, *Bio/technology* 7:147 (1989); D. J. Seikoe, *Ann. Rev. Neurosci.* 12:493 (1989); B. Muller-Hill, *Ann. Rev. Biochem.* 58:287 (1989); Neve, R. L. and H. Potter, in *Molecular Genetic Approaches to NeuropSychiatric Disease,* J. Brosius and R. Fremeau, Eds. (Academic Press, San Diego, in press); C. R. Abraham, et al., *Cell,* 52:487 (1988); C. R. Abraham, et al., *Neuroscience* 32:715 (1989)). Recently, it was found that the major component of the vascular amyloid in the Dutch variant of hereditary cerebral hemorrhage with amyloidosis (HCHWA-D) is the β-protein, not cystatin C, as in the Icelandic version (HCHWA-I), although the angiopathy appears similar (J. Ghiso, et al., *Proc. Natl. Acad. Sci.* 83:2974 (1986); S. G. van Duinen, et al., *Proc. Natl. Acad. Sci.* 84:5991 (1987)). When brain sections from individuals with this disease were analyzed by immunolabeling, ACT was also found to be present (M. M. Picken, et al., *Am. J. Pathol.* 134:749 (1989)). In contrast, amyloid deposits found in other diseases do not contain either β-protein or ACT. The biochemical characteristics of ACT and the β-protein suggest a basis for this special association. First, ACT is a serine protease inhibitor that functions by acting as a pseudosubstrate and binding covalently to its target protease to form a long-lived complex (J. Travis, et al., *Biochemistry* 17:5651 (1978)).

Second, an inspection of the sequence of the β-protein reveals a region near the N-terminus which shows a striking homology to one segment of the active site of serine proteases, including the key serine amino acid (FIG. 1) (E. Roberts, *Neurobiol. Aging* 7:561 (1986); Travis, J. and G. S. Salvesen, *Ann. Rev. Biochem* 52.:655 (1983); G. Salvesen, et al., *Biochemistry* 26:2289 (1987)). Thus, it seemed possible that ACT and β-protein might be able to form a complex by virtue of a protease inhibitor-like interaction and that this complex contributes to the stability of Alzheimer amyloid filaments. This hypothesis was tested, as described below. Results showed that, in fact, the β-protein is able to specifically bind stably to the inhibitory active site of ACT.

As described in Example 1, various synthetic peptides were tested for their effect on the inhibition of chymotrypsin by ACT in vitro.

Figure 2:
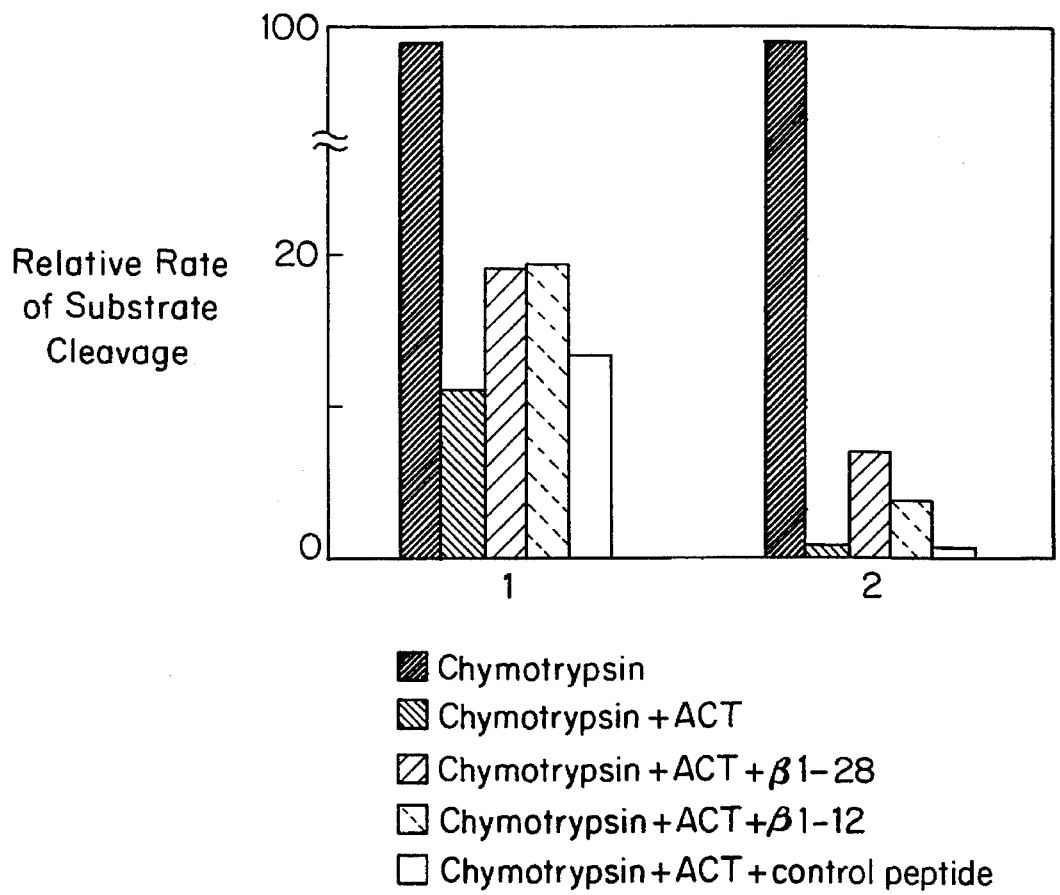
FIG. 2 is a graphic representation of the protease-like regulatory activity of Alzheimer amyloid β-protein.

FIG. 2 shows the results of assessment of the ability of ACT to inhibit protease activity; the assessment was carried out with the synthetic peptides. As shown in FIG. 2, when the ACT/chymotrypsin molar ratio was approximately 1:1, the ACT inhibited over 90 percent of the chymotrypsin activity. However, when ACT was pre-incubated with an approximately four-fold molar excess of synthetic peptides corresponding to amino acids 1–12 or 1–28 of the β-peptide prior to the addition of chymotrypsin, the inhibitory activity of ACT was substantially reduced and the chymotrypsin reaction rate increased 2 to 8-fold. In contrast, pre-incubation with even a 10-fold molar excess of a peptide corresponding to amino acids 258–277 of the β-protein precursor (which shows no similarity to the active site of serine proteases), failed to interfere with ACT. These data indicate that peptides showing similarity to the region around the key serine in the active site of serine proteases (FIG. 1), and in particular the Alzheimer amyloid β-protein, are able to interfere with the inhibitory function of a serine protease inhibitor, ACT. The specificity of the interaction indicates that it is occurring at the inhibitory active site of ACT. The fact that ACT still shows a substantial ability, even in the presence of the peptide, to inhibit chymotrypsin, probably reflects the fact that the binding of a protease inhibitor to its target involves many contacts with amino acids in the full protease active site which the small peptides naturally lack.

Figure 3:
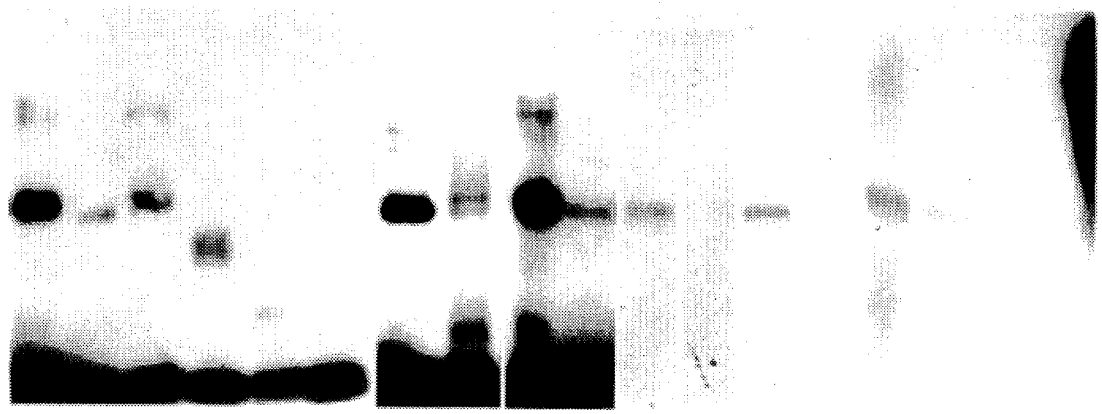
FIG. 3 shows the stable interaction of $\alpha_1$-antichymotrypsin and β-protein, demonstrated as described in Example 2.
Figure 3:
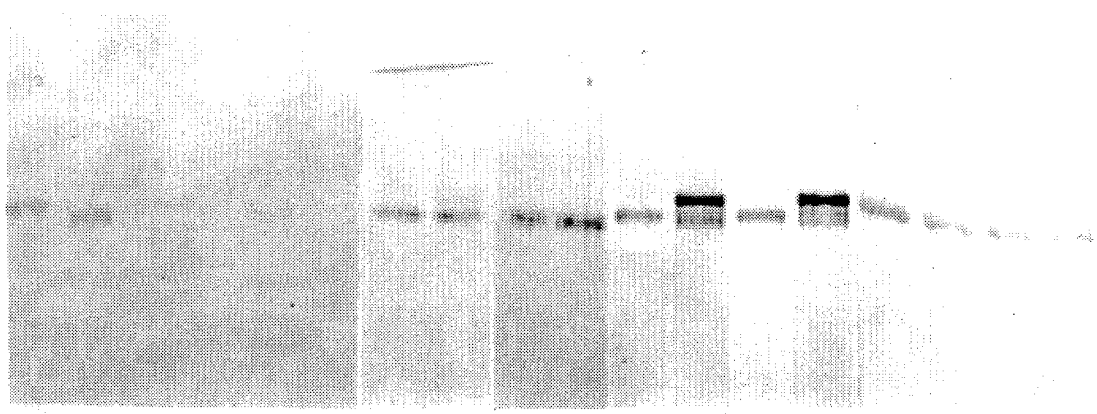

Assessment of the Stability and Specificity of Formation of the $\alpha_1$-ACT-β-Protein Complex Unlike true substrates that form a transient covalent intermediate with the protease through the hydroxyl group of its reactive serine, and then become cleaved as the bond breaks and the protease resumes its active state, protease inhibitors become cleaved, but only very slowly release their attachment to the protease (J. Travis, et al., *Biochemistry* 17:5651 (1978)). Thus, the inhibitors essentially inactivate the protease in a suicidal, stoichiometric interaction. The fact that serine protease inhibitors form stable complexes with their target proteases and that a serine protease inhibitor, ACT, is an integral component of the insoluble Alzheimer amyloid deposits, suggests that this protein might be incorporated into the filaments through a stable inhibitor-protease interaction. Therefore, the stability of the interaction between $\alpha_1$-antichymotrypsin and the β-protein was assessed. As described in Example 2, radioiodinated peptides corresponding to amino acids 1–12 and 1–28 of the β-protein and the unrelated segment 258–277 of the β-protein precursor were prepared, incubated in the presence of ACT under various conditions, and the mixture electrophoresed on SDS polyacrylamide gels. In the absence of ACT, the low M. W. peptides migrated rapidly at the dye front. However, in the presence of ACT, a radioactive band was generated at a position corresponding to a few thousand M. W. larger than the ACT protein (FIG. 3). Thus, the interaction first detected between ACT and the β-protein can be sufficiently stable to resist denaturation by boiling in SDS and β- mercaptoethanol. The indication that the ACT-β-protein interaction occurs at the protease inhibitory site of ACT was confirmed by the fact that the addition of chymotrypsin to ACT prior to the radioactive peptide prevented the formation of the ACT-peptide complex. Heat denaturation of ACT prior to the addition of the peptide also prevented complex formation.

The specificity of the $\alpha_1$-ACT-β-protein interaction was demonstrated by incubating the 1–28 peptide with other proteins (e.g., bovine serum albumin (BSA), creatine phosphokinase (CPK), carbonic anhydrase (CA), with which it failed to form stable complexes.

In sum, the work described indicates that the two components of the Alzheimer amyloid deposits—ACT and the β-protein—can associate in vitro to form an SDS-stable complex. The interaction is specific for both the peptide and the ACT protein, and likely occurs between the active protease inhibitor site of ACT and the N-terminus of the β-protein, which resembles the active site of serine proteases.

These results suggest a model for the structure of the Alzheimer amyloid filaments. The hydrophobic C-terminal portion of β-protein molecules making up the filament would be tucked into the interior, while the hydrophilic central segment (amino acids 12–28) would form the surface of the filament. The protease active site-related amino acids at the N-terminus would form an arm projecting from the surface of the filament and available for binding by ACT. However, the latter seems at least possible, inasmuch as the β-protein alone can form filaments in vitro having a β-pleated sheet conformation (D. A. Kirschner, et al., *Proc. Natl. Acad. Sci.* 83:503 (1986); E. M. Castano, et al., *Biochem. Biophys. Res. Comm.* 141:782 (1986); D. A. Kirschner, et al., *Proc. Natl. Acad. Sci.* 84:6953 (1987)). However, these filaments can easily be solubilized and therefore must lack a key component or structural conformation characteristic of true Alzheimer amyloid filaments. It is possible that the binding of a β-protein core filament to the relatively protease-resistant ACT provides the required extra stability.

These results also suggest a potential biological function for the β-protein. Since the β-protein can competitively interact with the active site of a serine protease inhibitor in vitro, it might be expected to be able to play a similar role in vivo. By decoying protease inhibitors (including the Kunitz-type inhibitor in the β-protein precursor), the β-protein, would serve as a protease enhancer-effectively increasing proteolytic activity in its vicinity. Overproduction of the β-protein, as would result, for instance, from increased proteolytic degradation of the β-protein precursor, could thus lead to a further increase in protease activity, with progressively adverse consequences.

Thus, as described herein, it has been shown that, in vitro, a serine protease inhibitor (ACT) interacts specifically with a serine protease-like target protein (Alzheimer β-protein) at a region of the latter which bears striking sequence homology to the active site of serine proteases, resulting in formation of a stable ACT-β-protein complex. The work described herein provides a reasonable molecular mechanism for formation of the insoluble protein filaments that comprise the amyloid deposits of Alzheimer's disease.

Assessment of Esterase Activity of β-protein, β-protein Fragments and β-protein Precursor Protein The β-protein and a β-protein precursor protein have been shown to have esterase activity, including cholinesterase activity, as described herein. This presumably results from the protease-like structure of the β-protein sequence shown in FIG. 1 inasmuch as proteases and esterases have a similar mechanism of action and a similar structure in their catalytic active sites.

The implications of the findings that the β-protein component of the amyloid protein present in Alzheimer's disease has esterase activity are more evident if one considers two facts about Alzheimer's disease. First, it has been shown that the majority of neurons affected in Alzheimer's disease are cholinergic. This fact has led to the formulation of the cholinergic hypothesis of pathogenesis. This hypothesis was the background for attempts to alleviate Alzheimer's disease symptoms with cholinergic drugs such as acetylcholinesterase inhibitors. As these drugs proved ineffective, the validity of the cholinergic hypothesis came into question. The other fact is that several researchers have demonstrated that neuritic plaques contain acetylcholinesterase activity when examined histochemically. It is now tempting to infer that the histochemically observed acetylcholinesterase activity is due to the activity of the peptides studied in vitro. The basis of this hypothesis is the fact that the β-protein is a major constituent of neuritic plaques and that true acetylcholinesterase has not been isolated from plaques or shown, by immunological assays, to be present in the plaques. It is reasonable to expect that the cholinesterase activity exhibited by these peptides might degrade acetylcholine at a faster rate than normal. Such excessive acetylcholine inactivation might compromise cholinergic input into receiving neurons, and result in degeneration. It is well known that neurons, including cholinergic neurons, when deprived of their afferent innervation, degenerate. Another possibility is that these peptides might also have protease activity that could directly destroy key proteins in the surrounding tissue.

Whatever the normal or pathologic functions of these peptides might turn out to be, designing compounds that selectively modify their observed activity is one strategy that might prove fruitful in the treatment of Alzheimer's disease. One explanation for the fact that researchers report conflicting results about the effectiveness of cholinergic treatment is that the inhibitors used were too non-specific to be used in a high enough concentration. After all, they were inhibitors of true acetylcholinesterase, which has many essential functions in the brain. It is quite possible that what is needed are inhibitors that inhibit the peptide cholinesterase activity but spare the true acetylcholinesterase. It is now possible to characterize the β-protein activity and identify and/or design inhibitors which act selectively to inhibit the β-protein while not affecting acetylcholinesterase activity. As shown in Example 4, inhibitors capable of preferentially inhibiting β-protein activity as compared with acetylcholinesterase activity have been identified.

Compounds and Methods for Interfering with ACT-β-protein Interactions and for Interfering with β-protein Esterase Activity As a result of the discovery of the specific interaction between ACT and Alzheimer β-protein, it is possible to design or select compositions or compounds which are useful to interfere with (reduce or prevent) this ACT-β- protein interaction. The discovery has also made possible a method of preventing the interaction in an individual and, thus, a method potentially useful for treating or preventing complex formation and adverse effects resulting therefrom. It provides a method of treating or preventing conditions, such as Alzheimer's disease, Down's syndrome and normal aging, in which ACT-β-protein complex is formed. It is also possible to design or select compounds which inhibit (reduce or eliminate) the esterase activity of the β-protein or otherwise render it inactive or ineffective. In one embodiment, the cholinesterase activity of the β-protein, β-protein precursor or β-protein fragment is inhibited or inactivated. In this embodiment, it may be desirable to interfere with or inactivate the β-protein cholinesterase activity specifically in an individual and not interfere with other enzymes which have similar beneficial activities, such as the "true" acetylcholinesterase. Such compositions or compounds useful in interfering with ACT-β-protein interaction or useful in inhibiting the β-protein esterase activity or otherwise rendering it inactive or ineffective; methods of interfering with ACT-β-protein interaction; methods of inhibiting the β-protein esterase activity or rendering it inactive or otherwise ineffective; and methods of administering such compounds or compositions to interfere with ACT-β-protein interaction or to inhibit β-protein esterase activity or render it ineffective are also the subject of the present invention. The compounds and method are particularly useful in reducing formation of ACT-β-protein complexes in individuals in whom such complexes form and result, directly or indirectly, in an abnormal or undesirable condition or a disease state. For example, such compounds can be used to reduce (totally or partially) or prevent formation of ACT-β-protein complexes in individuals who have Alzheimer's disease or would, without appropriate treatment, develop Alzheimer's disease.

Compounds of the present invention can be used to interfere with binding of ACT and Alzheimer's β-protein, either by binding to ACT, thus preventing formation of the ACT-β-protein complex, or by binding to β-protein, also preventing formation of the ACT-β-protein complex. For example, a peptide corresponding to all or a portion of the amino acid sequence of a serine protease, such as all or a portion of the sequence of the Alzheimer's β-protein can be used. Alternatively, a synthetic peptide which mimics the amino acid sequence of the inhibitory active site of ACT can be used to interfere with ACT-β-protein complex formation. This type of peptide will bind to the β-protein, resulting in the production of a synthetic peptide-β-protein complex and, in essence, will "tie up" β-protein, precluding the β-protein from interacting with ACT. It is also possible to identify compounds which interfere with (reduce or eliminate) ACT-β-protein complex formation and, thus, identify compounds useful for reducing or preventing complex formation. In the method of identifying a compound which interferes with complex formation, ACT, β-protein and a compound to be assessed for its ability to reduce or prevent complex formation are combined, under conditions suitable for complex formation. If the compound being assessed is one which interferes with ACT-β-protein interaction, complex formation will not occur or will occur to a lesser extent than would be the case if the compound were not present. The extent to which complex formation occurs is determined using known methods, such as that described in Example 2. Comparison of complex formation in the presence and absence (control conditions) of the compound being assessed is an indicator of the compound's ability to interfere (i.e., no difference in complex formation is an indication the compound is not able to interfere).

The peptide compounds of the present invention may have additional effects resulting from their influence, direct or indirect, on the protease inhibitor function of ACT. ACT is a serine protease inhibitor and Alzheimer's β-protein has been shown to inhibit ACT's ability to inhibit a serine protease (i.e., chymotrypsin). Thus, because it decoys protease inhibitors, β-protein enhances protease activity by effectively increasing proteolytic activity of other molecules (i.e., by reducing ACT's ability to inhibit serine proteases).

This view of the interaction between ACT and the β-protein suggests alternate outcomes from administration of the two types of peptide. In the case where the peptide binds to ACT to inhibit complex formation, the peptide may have an inhibitory effect on ACT, resulting in enhancement of protease activity, in a manner similar to that suggested for the β-protein itself. In the case in which the synthetic peptide mimics the inhibitory active site of ACT and binds to the β-protein, one might expect the opposite outcome. That is, the peptide would complex with the β-protein, preventing its interaction with ACT, and thus blocking the postulated protease enhancing effect of the β-protein. ACT then would be left free to exercise its function as a protease inhibitor.

A synthetic peptide of the present invention can be administered in a physiologically acceptable carrier (e.g., an appropriate buffer or physiologic saline solution) to an individual in whom ACT-β-protein complex formation is to be interfered with. It can be administered by any route via which it is possible to deliver a therapeutically effective quantity or dose to the individual in a form available to have the desired effect (reduction of complex formation). For example, a synthetic peptide of the present invention can be administered parenterally (e.g., intravenously or intramuscularly) in a composition which protects the peptide from degradation. It can be administered with another agent or drug, such as a drug used conventionally for treating the condition being treated or compounds of the present invention which inhibit β-protein enzymatic activity.

A synthetic peptide of the present invention can be made using known techniques, such as recombinant/genetic engineering techniques or chemical synthesis.

Characterization of β-protein activity has been carried out, as described herein, as to its esterase activity, including cholinesterase activity. In addition, other esterase activity (e.g., lipase activity) and protease activity of the β-protein can be assessed using known methods. For example, para-nitroanlide conjugated substrates designed to contain various peptide sequences can be synthesized and tested with the enzyme (Sarath, G. et al., "Protease assay methods" In: *Proteolytic Enzymes, a Practical Approach*, ed R. J. Beynon and J. S. Bond, IRL Press, Eynsham, 1989). Additional information about β-protein activity will provide guidance as to the type of inhibitors needed (e.g., esterase inhibitors, protease inhibitors).

Inhibitors can be identified using the β-protein, β-protein precursor protein and/or β-protein fragments, such as those described herein. In a method of identifying an appropriate inhibitor, β-protein, a substrate upon which β-protein has been shown to act (e.g., acetylthiocholine, paranitrophenyl acetate (PNPA)) and a potential inhibitor are combined, under conditions suitable for the β-protein to act upon the substrate (e.g., enzymatically to hydrolyze the acetylthiocholine or PNPA). If the agent being assessed is an inhibitor, β-protein activity will be less than β-protein activity in the absence of the agent being assessed. The activity can be determined using known methods. For example, in the case of an esterase inhibitor, which reduces the activity of the β-protein, the reduction in activity can be determined by measuring hydrolysis of a suitable substrate, such as PNPA. Similarly, in the case of an esterase inhibitor, such as a cholinesterase inhibitor, which reduces the activity of the β-protein, the reduction in activity can be determined by measuring hydrolysis of the substrate, such as acetylthiocholine. Less hydrolysis of the substrate in the presence of the agent being assessed than in its absence is an indication that the agent is an inhibitor. Inhibitors may be total or partial inhibitors. If assessment shows that β-protein has other enzymatic activity (e.g., other esterase activity or protease activity), appropriate inhibitors can be identified or designed using known methods. It is also possible to interfere with β-protein activity at the level of the β-protein precursor protein to prevent it from being processed into β-protein (thus, preventing it from forming an ACT-β-protein complex), in addition or instead of inhibiting its enzymatic activity.

Potential inhibitors can include known compounds such as protease, esterase, lipase, and cholinesterase inhibitors or compounds designed to have inhibitory activity. Once an inhibitor has been identified, or designed, it can be used as identified or designed or can be modified. For example, modifications that alter the partition coefficient, ionization and/or protein binding properties of an inhibitor can be carried out. Modifications of an inhibitor can serve to enhance its ability to (a) enter cells of the brain (cross the blood-brain barrier), (b) resist degradation by cellular enzymes, and/or (c) inhibit β-protein, for example. Compounds derived by such modifications can have enhanced inhibitory effect in the central nervous system and enhanced therapeutic efficacy.

For example, (p-amidinophenyl)methanesulfonyl fluoride (pAPMSF), which is commercially available and which has been shown herein to inhibit β-protein esterase activity, can be modified as described above. Candidate analogs include (p-amidinophenyl)ethanesulfonyl fluoride and (p-amidinoethyl benzyl)methanesulfonyl fluoride. These analogs can be synthesized using protocols similar to those described by Laura et al. for making pAPMSF and procedures of Wong and Shaw (Laura, R. et al., *Biochemistry*, 19:4859–4864 (1980); Wong, S. C. and Shaw, E., *Arch.. Biochem. Biophys.*, 161:536–543 (1974); Wong S. C. and Shaw, E. *Arch. Biochem. Biophys.*, 176:113–118 (1976)).

Ebelactone A has also been shown herein to inhibit β-protein esterase activity. Ebelactone A and Ebelactone B are commercially available. Analogs of these compounds, such as those having altered methylation can be designed. For example, 3,11-dihydroxy-4,6,8,10,12-pentamethyl-9-oxo-6-tetra-decenoic acid 1,3-lactone can be isolated from actinomycetes using the procedure of Umezawa et al. (Umezawa et al., *J. Antibiotics*, 33:1594–1596 (1980)). Alternatively, it may be obtained through chemical synthesis or derived from Ebelactone A by demethylation at carbon 2.

As with compounds useful for interfering with ACT-β-protein complex formation, compounds useful for inhibiting β-protein enzymatic activity can be administered to an individual in whom β-protein activity is to be inhibited (e.g, an individual with Alzheimer's disease). Such compounds can be administered in a pharmaceutically acceptable carrier, such as an appropriate buffer or physiological saline solution. They will be administered by any suitable route by which it is possible to deliver a therapeutically effective quantity or dose to the individual in a form available to have the desired effect (inhibition, total or partial, of β-protein enzymatic activity, such as esterase or protease activity). It can be administered parenterally (e.g., intravenously or intramuscularly). It can be administered with another agent or drug, such as a synthetic peptide of the present invention which interferes with ACT-β-protein complex formation.

The discovery described herein also makes it possible to identify ACT-β-protein complexes in tissue obtained from an individual, such as in biopsy tissues obtained from an individual suspected of having abnormally high levels of the complexes. This can be used, for example, to determine the presence or absence and, if desired, the quantity of ACT-β-protein complexes in brain tissue obtained at autopsy.

The present invention will now be illustrated by the following examples, which are not intended to be limiting in any way.

EXAMPLE 1

Assessment of the Protease Regulatory Activity of Alzheimer β-Protein

Various synthetic peptides were tested for their effect on the inhibition of chymotrypsin by ACT in vitro. The synthetic peptides tested were:

1. a peptide corresponding to amino acids 1–28 of the N-terminal portion of the Alzheimer β protein (See FIG. 1).
2. a peptide corresponding to amino acids 1–12 of the N-terminal portion of the Alzheimer β protein (See FIG. 1, first 12 amino acids); and
3. a control peptide corresponding to amino acids 258–277 of the Alzheimer β-protein precursor, which does not show any similarity to the serine protease active region sequence.

The activity of chymotrypsin was measured by cleavage of the chromogenic substrate Succinyl-Ala-Ala-Pro-Phe-nitroanilide. Results showed that chymotrypsin activity is reduced about 90 percent in the presence of an approximate equal molar concentration of ACT. If a four-fold molar excess of either of the two synthetic peptides from the N-terminal portion of the β-protein (corresponding to amino acids 1–28 and 1–12 respectively) is added to ACT prior to the protease assay, the peptide interferes with the inhibitory activity of ACT. In contrast, the control peptide corresponding to amino acids 258–277 of the β-protein precursor does not modulate ACT's ability to inhibit chymotrypsin.

Results are shown in FIG. 2. The data shown for each graph represent the average of four independent assays in which 0.5 (left) or 0.6 (right) µg of ACT were incubated for 2 min±peptide in 10 µl 0.1 M phosphate buffer, pH 7, at 20° C. prior to the addition of 0.3 µg of chymotrypsin. After a further incubation of 2 min, the reaction volume was increased to 0.8 ml, 15 µl of 2 mg/ml substrate was added and the reaction followed at OD 405 for five minutes. The graphs compare the relative slopes of the reaction curves (all straight lines) normalized to the reaction rate of chymotrypsin alone. The peptides did not have any independent effect on chymotrypsin.

EXAMPLE 2

Assessment of the Stability of Interaction Between α-antichymotrypsin and β-protein The ability of synthetic fragments of β-protein to inhibit ACT (FIG. 2) indicates that at least a transient complex can form between the two proteins. The stability of such complexes was demonstrated by incubating ACT with radiolabeled β-protein fragments under various conditions, and then analyzing the complex formation by polyacrylamide gel electrophoresis. In some experiments, a protein cross-linking agent (DSS) was used to stabilize the complex prior to gel electrophoresis (FIG. 3, lanes 1–6, 8–11). However, even in the absence of cross-linking, a complex is formed which is stable to boiling in SDS and β-mercaptoethanol (FIG. 3, lanes 7, 12 and 13). The addition of an equal molar amount of chymotrypsin to ACT blocks the active site and prevents the complex formation (FIG. 3, lanes 5, 10, 11, 14 and 15). Denaturing the ACT protein by heat (FIG. 3, lane 3) also prevents the complex formation. Immunostaining of the blotted protein with antibodies to $\alpha_1$-antichymotrypsin (FIG. 3, lower panel) indicated that neither the heat nor the chymotrypsin treatment destroyed the ACT. Thin layer chromatography confirmed that the amount of chymotrypsin added to the ACT was not sufficient to digest the peptide.

EXAMPLE 3

Characterization of Esterase Activity of β-protein, β-protein precursors and β-protein Fragments Because of the structural similarities between β-protein and the active site of serine proteases/esterases, and the finding that ACT binds to β-protein, experiments were carried out to examine whether the β-protein, its precursors, or fragments of it exhibited any esterase or protease activity. The peptides were synthesized to correspond to different lengths of amino acids and three well-characterized forms of amyloid precursor proteins referred to as APP751, APP770 and APP695, were used. They were obtained from Dr. Barry Greenberg (Upjohn, Kalamazoo, Mich.) purified from a bacculovirus expression system. The relative levels of these three proteins are altered in Alzheimer's Disease (Neve, R. L. and H. Potter, in *Molecular Genetic Approaches to Neuropsychiatric Disease,* J. Brosius and R. Fremeau, Eds. (Academic Press, San Diego). The main protein in the brain is believed to be the APP695 protein, which differs from APP751 and APP770 in that it lacks a domain with protease/esterase inhibitory function.

Various ester and peptide substrates were tested under different conditions. When the peptides were incubated with acetylthiocholine iodide or butyrylthiocholine iodide using a modified acetylcholinesterase assay (Ellman, G. L. et al., *Biochem, Pharmacol* 7:88–95 (1961), Gorun, V. et al. *Anal. Biochem.* 86:324–326 (1978)), the following results were observed. The AAP751 and AAP770 proteins (β-protein precursor proteins) did not hydrolyze either substrate significantly. On the other hand, the AAP695 peptide hydrolyzed both substrates. It had a specific activity of 4–6 nmol/min/mg using acetylthiocholine as substrate, and 1.8 nmol/min/mg using butyrylthiocholine as substrate. A peptide comprised of 1–28 amino acids of the β-protein had a specific activity of 0.5–1.4 nmol/min/mg with acetylthiocholine versus 1.1 nmol/min/mg with butyrylthiocholine as substrates. This result indicates that the β protein esterase is different than either acetylcholinesterase or butyrylcholinesterase, each of which strongly prefer their own specific substrates. These values were consistent in repeated experiments using different batches of the peptides.

To determine whether the observed activity in APP695 was due to a true esteratic action rather than a nonspecific protein action, its activity was compared to that observed with cathepsin G, a serine protease, which hydrolyzed either acetylthiocholine or butyrylthiocholine only minimally, but still favored the butyrylthiocholine to acetylthiocholine.

When the APP695 protein was inhibited with either physostigmine or DFP, it showed 58% and 70% inhibition, respectively of its ability to hydrolyze acetylthiocholine. The inhibitors were added to the AAP695 protein 15 minutes prior to the addition of the substrate. The standard assay for esterase activity was then carried out as above. The amount of inhibitors used was sufficient to completely inhibit a much higher activity of erythrocyte acetylcholinesterase. The latter finding indicates that the activity observed is not due to an impurity of true acetylcholinesterase, which would have been otherwise inhibited by the concentration of inhibitors used. Finally, when the precursors were electrophoresed on SDS-PAGE and silver stained, only one major band was observed, which is consistent with there being only one major precursor protein.

One reason this activity has not been reported earlier is the possibility that a different source of APP might have been used. APP expressed in a bacterial system would differ from APP expressed in this eukaryotic system in that the bacterially expressed APP is unglycosylated. More importantly, the assay described and used herein for acetylcholinesterase measurement is performed at higher concentrations of enzyme and is more sensitive than standard techniques.

Figure 4:
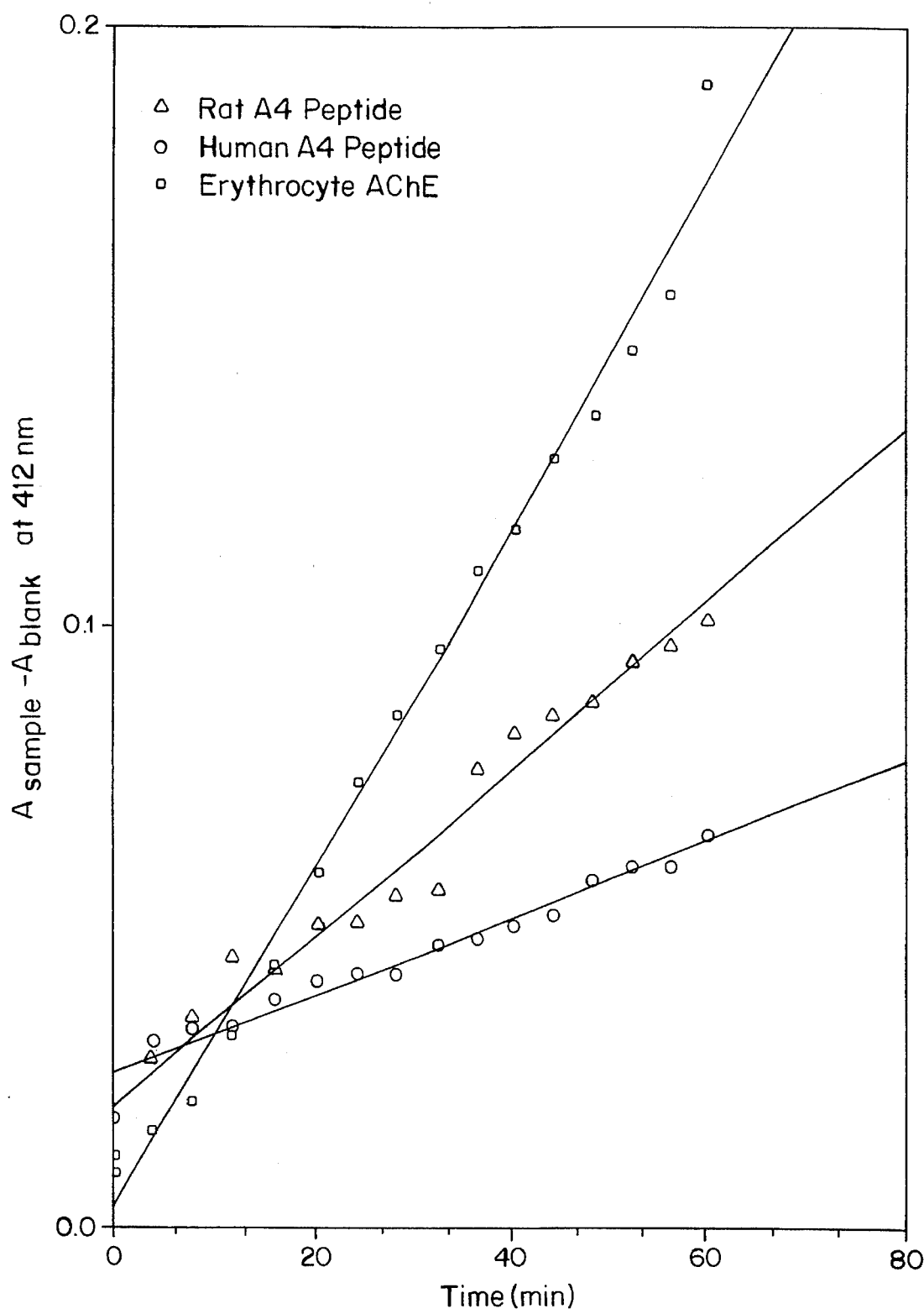
FIG. 4 is a graphic representation of the time course of hydrolysis of acetylthiocholine iodide by rat β-peptide 1–40 (5 μg), human β-peptide 1–40 (5 μg) and acetylcholinesterase (0.0025 μg).

Experiments using synthetic Alzheimer β-peptides 1–40 corresponding to rat and human sequences were performed to measure the time course of hydrolysis of acetylthiocholine iodide. FIG. 4 shows the results obtained. The results indicate that both peptides hydrolyze acetylthiocholine in a time-dependent manner.

HPLC-pure synthetic 1–40 peptide and 40-1 reverse peptide, obtained from Dr. Bruce Yankner, were used to test whether the esterase activity observed was due to an intrinsic property of the β-peptide and not to a non-specific peptide action. The peptides can also be produced using known methods (e.g., they can be synthesized chemically). The reverse peptide contains exactly the same amino acids as the 1–40 except that they are in the reverse order from the carboxy terminal to the amino terminal. If the esterase action of the peptide were due to non-specific action, then the arrangement of the amino acids would not be expected to affect it significantly. However, if it were a true enzyme, then the arrangement of the amino acids is of key importance to its action. Preliminary experiments with these peptides have indicated that the 1–40 β-peptide has an activity of 0.26 mU (nmol/min/mg). The reverse peptide had ¼ that activity but with a high standard deviation such that it is not likely to be real. The latter point is confirmed by an inhibition experiment in which DFP (a classical serine esterase/protease inhibitor) inhibited the activity of the 1–40 peptide by 75%, but had no effect on the activity of the reverse 40-1 peptide.

Radiolabeling experiments indicate that the APP695 becomes preferentially labeled with [3H]-DFP as compared to APP751 or APP770. The label is at the position of the major protein band and does not comigrate with acetylcholinesterase on SDS-PAGE. The significance of this finding is that it corroborates the observed results with esterase activity: both the activity data and the radiolabeling data indicate that the esterase enzyme observed is not acetylcholinesterase. Finally, the labeling of the major APP695 band and not of the major bands of other APP species 751 and 770 argues against the DFP-binding protein being an impurity, particularly since all precursor proteins were purified in a similar manner.

EXAMPLE 4

Identification of Inhibitors of β-Protein Function

Two inhibitors of the esterase activity of β-protein were identified according to the present invention. These inhibitors display preferential inhibition of β-protein activity as compared with acetylcholinesterase activity.

A) Inhibition of β-Protein Activity by para-Amidinophenylmethanesulfonyl fluoride (pAPMSF)

p-nitrophenyl acetate (PNPA) is a substrate for a variety of esterases, including acetylcholinesterases and other esterases. This substrate was selected as a substrate for β-protein. In particular, amyloid precursor protein (APP695), purified from Chinese hamster ovary cells, was tested for its ability to hydrolyze PNPA. APP695 was purified from Chinese hamster ovary cells (CHO cells) essentially as described (Lowery, D. E. et al., *J. Biol. Chem.*, 266: 19842–19850 (1991)). These studies indicated that the APP695-associated esterase can hydrolyze this substrate.

Next, assays were conducted using APP695 and PNPA to identify inhibitors of the reaction. Para-amidino-phenylmethanesulfonyl fluoride (4-amidinophenylmethanesulfonyl fluoride; pAPMSF; Boehringer Mannheim, Indianapolis, Ind.), a known inhibitor of certain serine proteases was selected as a potential inhibitor. Aliquots of CHO cell-derived APP695 (5 μl containing 0.9 μg) were incubated in the presence or absence of para-amidinophenylmethanesulfonyl fluoride (5 mM), in a final volume of 20 μl Na/phosphate (20 mM, pH 7.0), for 1 hour at room temperature. Secondly, 20 μl of p-nitrophenyl acetate (PNPA) in phosphate buffer at concentrations of 1, 2, 4, or 8 mM was added and mixed with the samples with or without pAPMSF. The progress of the reactions was monitored spectrophotometrically. Absorbance at 405 nm was read and recorded using an ELISA plate reader over a period of time. A set of blanks composed of each component, minus the protein, was prepared in parallel. For kinetic analyses, the difference between sample and the corresponding blank was used.

The results of this study indicated that p-amidinophenylmethanesulfonyl fluoride (pAPMSF) inhibits the APP695-associated esterase activity by up to 70%. The data were subjected to Lineweaver-Burk analyses (see FIG. 5), and the results of this analysis suggest that inhibition is competitive.

B) Inhibition of β-Protein Activity by Ebelactone A and Ebelactone B

Ebelactone A and Ebelactone B (CalBiochem, La Jolla, Calif.), which are known inhibitors of certain esterase, lipase and N-formylmethionine aminopeptidase activities, were selected as potential inhibitors. Ebelactone A and B were tested for their ability to inhibit amyloid precursor protein-associated esterase activity. Membrane fractions containing APP695 were obtained from CH0695 cells essentially as described (Yoshikawa et al., *Nature* 459: 64–67 (1992)). CH0695 cells are CHO cells which have been transfected with a clone which encodes APP695 and which directs the overexpression of APP695. Aliquots (5 μ) of membrane fractions from APP695 expressing CHO cells (CH0695) or mock-transfected control cells (TH-8) were incubated in the presence or absence of each of the following: Ebelactone A (2.6 mM), Ebelactone B (2.5 mM), or DFP (10 mM diisopropyl fluorophosphate; Sigma Chemical Company, St. Louis, Mo.) in a final volume of 10 μl Na/Phosphate (20 mM, pH 7.4) for 20 minutes at 37° C. Next, 10 μl of acetylthiocholine iodide (4 mM) in phosphate buffer were mixed with the samples and incubated for 85 minutes. At the end of the incubation, 250 μl dithionitrobenzoic acid (DTNB) were added to each sample to stop the reaction and the absorbance at 405 nm was read and recorded using an ELISA plate reader. The blanks were initially composed of every component minus the corresponding membrane sample. The corresponding membrane samples were added to the appropriate blanks after stopping the reaction with DTNB. For activity determination, the difference between each sample and the corresponding blank was used. The same experiment was performed on purified APPs from a bacculovirus expression system (Lowery et al., *J. Biol. Chem.*, 266:19842–19850 (1991)), except that preincubation with inhibitors was for 1 hour, and incubation with substrate was for 55 minutes.

The membrane fractions from CHO cells overexpressing APP695 had an activity of 6.9 nmol/min/mg versus 2.2 for the TH-8 controls. Ebelactone A did not inhibit the activity of membrane fractions from TH-8 cells, while it completely inhibited the activity of membrane fractions from CH0695 cells. Ebelactone A also inhibited bovine erythrocyte acetylcholinesterase (ACHE) by 12%. In contrast, Ebelactone B did not inhibit the activity of any of the membrane fractions, while it inhibited AChE activity by 62%. DFP inhibited the activity of membrane fractions from control TH-8 cells by 5% and from CH0695 cells by 87%. DFP completely inhibited AChE activity.

Similar results were obtained when APP695 was purified from a bacculovirus expression system. In particular, Ebelactone A inhibited APP695-associated esterase activity by >90%. In contrast, under the conditions of the experiment, APP695-associated esterase activity was not inhibited by Ebelactone B. In addition, under the conditions of the experiment, no inhibition of APP751-associated esterase activity by Ebelactone A was observed, and Ebelactone B gave an abnormally high blank with APP751 such that inhibition could not be determined. Again, AChE activity was more susceptible to inhibition by Ebelactone B (86%) than Ebelactone A (56%). The latter result is consistent with the results of the first experiment, considering the different times of pre-incubation with inhibitor (20 minutes versus 60 minutes).

These results suggest that Ebelactone A has specific inhibitory activity against APP-associated esterase activity, which is of significance in the diagnosis, study, and treatment of Alzheimer's Disease.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting enzymatic activity of Alzheimer amyloid β-protein, comprising contacting Alzheimer amyloid β-protein with an amount of a compound effective to inhibit enzymatic activity of Alzheimer amyloid β-protein, wherein the compound is selected from the group consisting of para-amidinophenylmethanesulfonyl fluoride and Ebelactone A.

2. The method of claim 1, wherein the enzymatic activity of Alzheimer amyloid β-protein is an esterase activity selected from the group consisting of cholinesterase activity and lipase activity.

3. The method of claim 2, wherein the compound is a compound which inhibits cholinesterase activity.

4. The method of claim 2 wherein the compound which inhibits esterase activity is a compound which inhibits lipase activity.

\* \* \* \* \*